United States Patent [19]

Trestianu et al.

[11] Patent Number: 4,762,981

[45] Date of Patent: Aug. 9, 1988

[54] HEATING DEVICE IN PARTICULAR FOR AUTOMATIC SAMPLERS

[75] Inventors: Sorin Trestianu, Rodano Millepini; Bruno Tosi, Carate Brianza, both of Italy

[73] Assignee: Carlo Erba Strumentazione S.p.A., Italy

[21] Appl. No.: 22,410

[22] Filed: Mar. 6, 1987

[30] Foreign Application Priority Data

Mar. 7, 1986 [IT]   Italy ............................... 21158/86[U]

[51] Int. Cl.⁴ .............................................. H05B 3/62
[52] U.S. Cl. ................................... 219/400; 126/21 A
[58] Field of Search ........... 219/400; 126/21 A, 21 R; 34/202, 235, 195, 197, 215, 210, 233

[56] References Cited

U.S. PATENT DOCUMENTS

| | | | |
|---|---|---|---|
| 2,412,407 | 12/1946 | Kilbury | 34/197 |
| 3,612,032 | 10/1971 | Kweller | 126/21 A |
| 3,626,922 | 12/1971 | Borge | 126/21 A |
| 3,926,171 | 12/1975 | Kurek | 126/21 A |
| 4,431,889 | 2/1984 | Saponara | 126/21 A |
| 4,621,439 | 11/1986 | Maw-Chyi | 34/233 |
| 4,654,508 | 3/1987 | Logel | 219/400 |

Primary Examiner—E. A. Goldberg
Assistant Examiner—Teresa J. Walberg
Attorney, Agent, or Firm—Lerner, David, Littenberg, Krumholz & Mentlik

[57] ABSTRACT

A device for heating sample containing vials, in a gas-chromatographic apparatus provided with an automatic sampler, which includes a shroud in which a depression is made by a fan which sucks external air and conveys it under pressure into a Venturi tube shaped duct. This depression causes more external air to be sucked through separate openings of the shroud and to follow a different path along the resistors, the sampler, the tray and the vials and to be eventually exhausted through the vent together with air coming from the fan duct.

15 Claims, 2 Drawing Sheets

HEATING DEVICE IN PARTICULAR FOR AUTOMATIC SAMPLERS

BACKGROUND OF THE INVENTION

1. Field of the Invention

The present invention concerns a device for heating vials containing samples and relevant solvents to be submitted to chromatographic analysis, as well as in case at least part of the sampling apparatus, in automatic samples for gas chromatography.

These automatic samplers comprise a series of test-tubes or vials, each containing a sample generally diluted in a relevant solvent, accommodated on a tray which drives them in succession to a drawing station. Here, a needle penetrates through the vial sealing septum and draws an amount of liquid (sample+possible solvent) of same, transferring it to the injector of a chromatograph.

2. Description of the Prior Art

Solvents used in gas chromatography are usually very volatile, with boiling points generally between 35° and 70° C. and considerable vapour tension even at room temperature. Furthermore, due to the sample characteristics of viscosity or solubility in the solvent used, it is often necessary to heat the vials and possibly the sample path inside the sampler almost as far as the chromatograph, at temperatures approaching the solvent boiling point. Heating must obviously be as much as possible controlled in temperature and homogeneous.

Solvents used are often flammable and/or toxic, it is therefore very important that solvent vapours escaping from the vial pierced septa do not stagnate in the ambient, but are removed and diluted with air or other gases so that they do not reach explosive and/or toxic concentrations.

OBJECTS OF THE INVENTION

The described characteristics and working conditions of automatic samples for gas chromatography involve a series of requirements for the heating of vials and at least part of the sampler; said requirements are met with the invention disclosed in the present application. Summarizing, said requirements are the following:

(a) As heating must be substantially uniform at substantially homogeneous temperature and must involve not only the vials but also at least part of the sample path in the sampler, it must be performed by convection through a gaseous fluid.

(b) The gaseous fluid (in practice air) path must be such as to provide the required control and the desired substantial temperature uniformity.

(c) Said path must be such as to ensure that heated air after crossing the area with the vials, is immediately vented to the outside of the apparatus in order to avoid that explosive and/or toxic solvent concentrations in the air are reached as result of air recirculation.

(d) Finally, the air carrying the solvent vapours collected near the vials must not come into contact with non protected electrical heaters or devices and in particular with the fan motor which causes its circulation.

(e) It must be added that the air path, considering the characteristics of the sampling system, cannot be completely airtight with respect to the outside.

(f) For the reasons mentioned in the preceding points, it is not advisable to feature a closed-cycle air circulation.

SUMMARY OF THE INVENTION

In order to comply with all said requirements, the present invention concerns a device for heating the vials containing the samples and relevant solvents to be submitted to chromatographic analysis, as well as in case at least part of the sampling apparatus, in automatic samplers for gas chromatography, characterized in that it comprises: a shroud housing the parts to be heated; means to create and maintain a depression inside the shroud by sucking air from same and transferring it to a waste duct; one or more air inlets to such ambient air into the shroud; one or more heating elements for sucked ambient air; and deflectors for defining one or more paths for the sucked and heated ambient air, starting from the air inlets up to the waste duct, the path allowing air to pass only once in contact with the sample vials.

In particular, it is very advantageous that the means to create and maintain a depression inside the shroud consists of a Venturi tube arranged in a duct fed with ambient air under the action of a sucking fan and having the same waste line with the flow or flows of the heated air.

BRIEF DESCRIPTION OF THE DRAWINGS

These and other characteristics of the present invention will now be described by way of illustrative example with reference to the accompanying drawings, where.

DESCRIPTION OF THE PREFERRED EMBODIMENT

Figure 1:
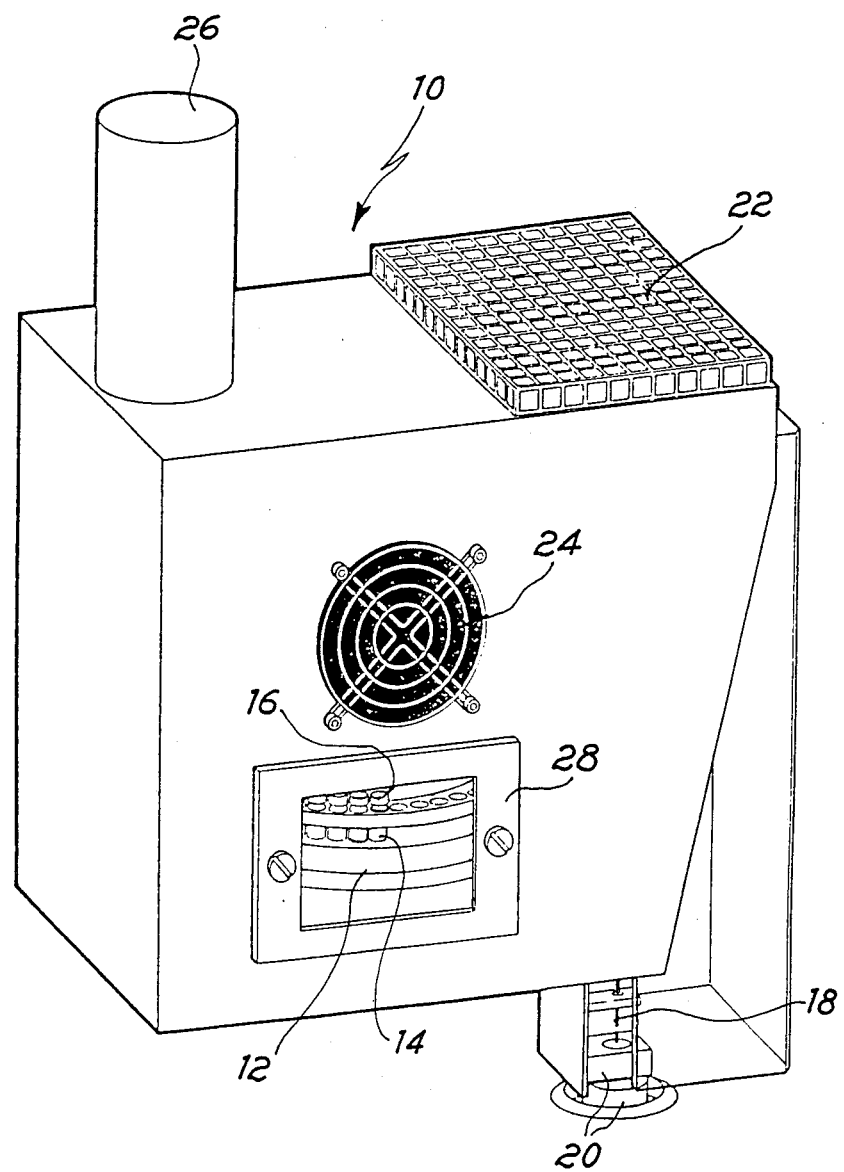
FIG. 1 is a perspective view of the device according to the invention assembled on an automatic sampler for gas chromatography.

The heating device according to the invention comprises a shroud 10 having a substantially box-shaped configuration and being substantially closed, where a tray 12 is housed accommodating a series of test-tubes or vials 14 sealed on the top by a septum 16 and containing a series of samples, generally diluted with an appropriate solvent. The box-shaped shroud 10 also accommodates the sampling apparatus, here not detailedly illustrated as it is known in itself, which comprises a device to draw the samples from each single vial in correspondence with a drawing station to which the tray 12 drives in succession all the vials 14, as well as an injection syringe, more thoroughly visible in FIG. 2 and illustrated at 18, which can introduce its end into an injection part 20 of a gas chromatograph.

Externally the box-shaped housing is characterized in that its presents one or more inlets 22 for ambient air intended for samples heating, at least one opening 24 for air induction into the system which creates the depression inside the shroud, as well as a single venting duct 26 common to the path of the air sucked through the inlets 22 and to the path of the air sucked through the opening 24, as it will be better described hereinafter with reference to FIG. 2.

The side wall of the box-shaped shroud 10 can be provided with a small port 28 for inspection and access to the vial supporting tray 12.

Figure 2:
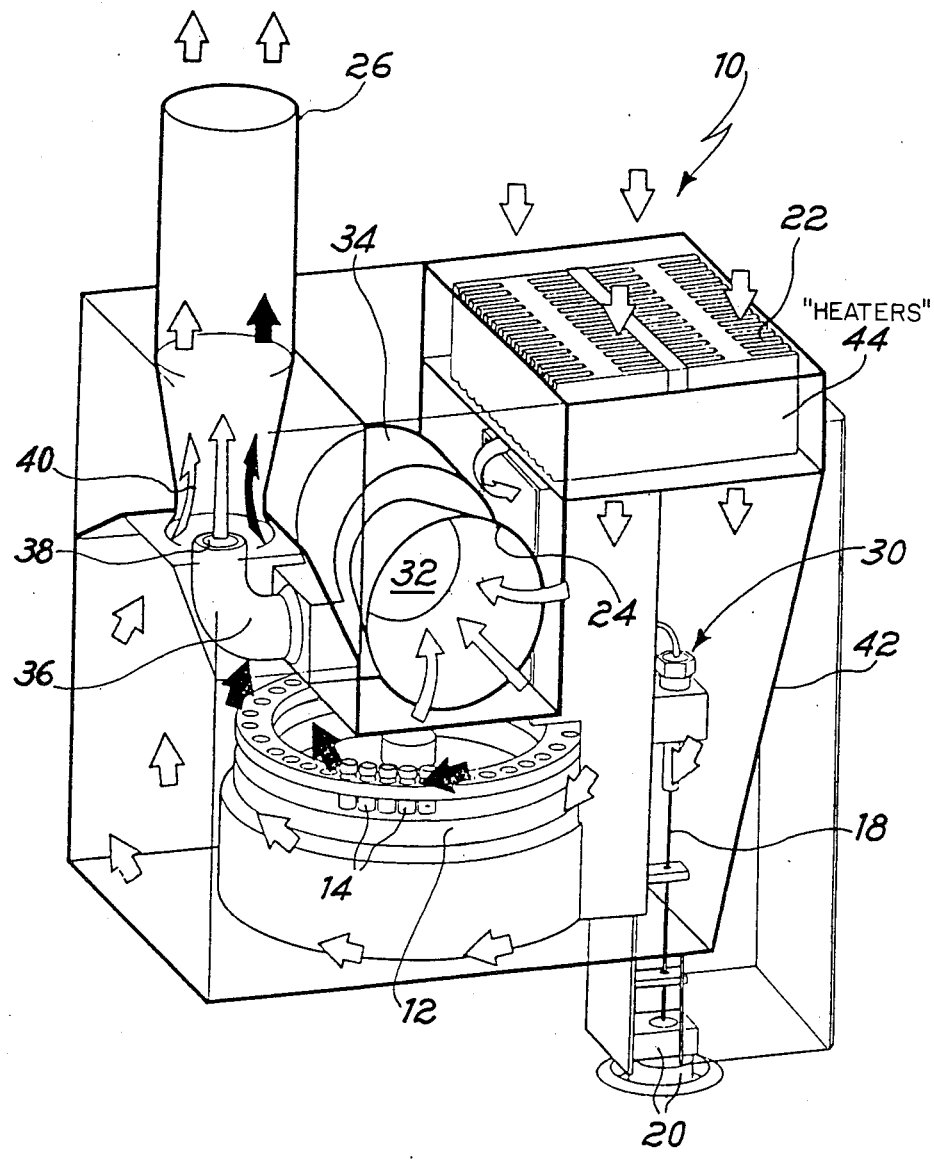
FIG. 2 is a perspective view with certain parts removed and in split section to show the components of the heating device.

FIG. 2 better shows the two air flows provided in the heating device, the first one for the apparatus which creates depression inside the box-shaped shroud 10, and the second one for the flow of air which is heating the vials 14, the tray 12 supporting them and at least part of the sampling system, which can be partially seen and is illustrated at 30 in FIG. 2.

The first air flow features a suction at the opening 24 and air conveyance within a duct 32 under the action of a fan, not shown, placed in a housing 34, for instance appropriately screw-shaped. The latter conveys the air sucked and put under pressure by the fan into a duct 36 having an opening 38 which leads to a shaped section 40 forming a Venturi tube ejection duct, known in itself, leading to the vent 26. The speed of air escaping through the opening 38 generates a depression in the ejection duct 40 which allows air suction from an ambient connected to the same. Said ambient is defined by a second air path, independent from the first one as far as the ejector 40 and comprising the openings 22 for external air intake, one or more deflectors, for example such as illustrated at 42, to define a path of said air inside the shroud 10, and an outlet to the ejector 40. Said second air path is such as to feature the passage of air in correspondence with the vials 14 and then the immediate conveyance of said air to the vent, so as to remove and eliminate all vapours forming above and near the vials 14 due to septa piercing, vapours which as previously stated can be flammable and/or toxic. Heating is performed by means of suitable elements, for example resistors which are housed in an appropriate seat 44 immediately downstream of air intakes 22. Air is therefore immediately heated and yields its heat both to the sampler 30 and to the tray 12 and vials 14, and thereafter it is immediately conveyed to the ejector 40 and exhausted to the ambient through the vent 26, thus ensuring, on one side, that vials 14 are sufficiently heated and, on the other, that levels of dangerous concentration of solvent vapours are not reached in the ambient from the standpoints of flammability and toxicity.

Temperature setting is performed by acting on the resistors placed in the seat 44, while air delivery through the path 24, 32, 34, 36 and 38 is preferably kept constant in order to maintain depression inside the housing 10 constant as well. The latter cannot be completely airtight with respect to the outside, in that it is necessary, in addition to intakes 22 and 24, to have a small port near the injector 20 for reasons of practical configuration of the equipment. However, air entering through said port is heated due to the injector heating and therefore it does not change the thermal conditions of the vials and/or the sampling device. The device is provided with safety systems. In particular there is a safety which disconnects the resistors placed in the seat 44 in case the fan inside the housing 34 stops working for any reason whatever. Another safety system keeps the resistors temperature at a lower value than the inflammability point of that solvent, among the solvents used, which has the lower value of said inflammability point.

We claim:

1. Apparatus for providing heated samples to a predetermined location for chromatographic analysis comprising shroud means, sampling means within said shroud means, said sampling means including sample storage means for storing a plurality of samples and sample handling means for transporting said plurality of samples between said sample storage means and said predetermined location, said shroud means including air intake means for permitting entry of ambient air into said shroud means, heating means for heating said ambient air within said shroud means, venting means for venting said heated ambient air from said shroud means, air conducting means for conducting a flow of said ambient air from said air intake means and said heating means to said venting means, and air directing means for directing said flow of ambient air from said heating means directly to said venting means in a manner such that said flow of ambient air travels past said sample handling means and said sample storage means thereby heating said samples in said sample handling means and said sample storage means and removing any gases generated therein.

2. The apparatus of claim 1 wherein said air conducting means includes pressure reduction means for reducing the pressure in said shroud means adjacent to said venting means so as to create said flow of ambient air towards said venting means.

3. The apparatus of claim 2 wherein said pressure reduction means comprises venturi means and secondary air flow means for creating a secondary flow of air through said venturi means.

4. The apparatus of claim 3 wherein said secondary air flow means includes fan means and first conduit means for directing said secondary flow of air from said fan means to said venturi means, and wherein said venturi means includes second conduit means connected to said venting means.

5. The apparatus of claim 4 wherein said first conduit means directs said secondary flow of air in a direction substantially parallel to said second conduit means, and wherein said second conduit means includes entry means for permitting said flow of ambient air to be drawn into said second conduit means by said secondary flow of air in said first conduit means.

6. The apparatus of claim 5 wherein said first conduit means and said second conduit means are concentrically disposed with respect to each other.

7. The apparatus of claim 1 wherein said heating means comprises adjustable resistor means.

8. The apparatus of claim 2 wherein said heating means comprises adjustable resistor means, and further including sensing means for sensing said reduced pressure in said shroud means, and disconnect means for disconnecting said adjustable resistor means in response to said sensing means sensing a predetermined reduced pressure in said shroud means.

9. The apparatus of claim 7 or 8 wherein said heating means further comprises temperature control means for maintaining said adjustable resistor means at a predetermined temperature.

10. The apparatus of claim 9 wherein said temperature control means includes sensing means for sensing the temperature within said shroud means, and disconnect means for disconnecting said adjustable resistor means in response to said temperature sensing means sensing a temperature above a predetermined temperature value.

11. Apparatus for providing heated samples including a volatile solvent to a predetermined location for chromatographic analysis comprising shroud means, sampling means within said shroud means, said sampling means including sample storage means for storing a plurality of said samples and sample handling means for transporting said plurality of samples between said sample storage means and said predetermined location, said shroud means including air intake means for permitting entry of ambient air into said shroud means, heating means comprising adjustable resistor means for heating said ambient air within said shroud means, temperature control means for controlling the temperature provided by said adjustable resistor means so as to maintain said temperature below the flammability point of said volatile solvent, venting means for venting said heated ambient air from said shroud means, air conducting means for conducting a flow of ambient air from said air intake means and said heating means to said venting means, said air conducting means including pressure reduction means for reducing the pressure in said shroud means adjacent to said venting means so as to create said flow of ambient air toward said venting means, air directing means for directing said flow of ambient air from said heating means directly to said venting means in a manner such that said flow of ambient air travels past said sample handling means and said sample storage means thereby heating said samples in said sample handling means and said sample storage means and carrying any volatile gases produced by said volatile solvent therefrom directly to said venting means, sensing means for sensing said reduced pressure in said shroud means, and disconnect means for disconnecting said adjustable resistor means in response to said sensing means sensing a predetermined reduced pressure in said shroud means.

12. The apparatus of claim 11 wherein said pressure reduction means comprises venturi means and secondary air flow means for creating a secondary flow of air through said venturi means.

13. The apparatus of claim 12 wherein said secondary air flow means includes fan means and first conduit means for directing said secondary flow of air from said fan means to said venting means, and wherein said venturi means includes second conduit means corresponding with said venting means.

14. The apparatus of claim 13 wherein said first conduit means directs said secondary flow of air in a direction substantially parallel to said second conduit means, and wherein said second conduit means includes entry means for permitting said flow of ambient air to be drawn into said second conduit means by said secondary flow of air.

15. The apparatus of claim 14 wherein said first and second conduit means are concentric with respect to each other.

* * * * *